United States Patent [19]

Fecht

[11] Patent Number: 4,795,446

[45] Date of Patent: Jan. 3, 1989

[54] MEDICAL TUBE DEVICE

[75] Inventor: David C. Fecht, Manchester, Mo.

[73] Assignee: Sherwood Medical Company, St. Louis, Mo.

[21] Appl. No.: 823,918

[22] Filed: Jan. 30, 1986

[51] Int. Cl.[4] .............................................. A61M 5/00
[52] U.S. Cl. .................................... 604/264; 604/273; 604/275; 604/239
[58] Field of Search ........................ 604/4, 53, 93, 104, 604/117, 264, 273, 275, 280, 282, 239, 174, 270, 272, 274, 411–414, 122; 128/1 D, 343, 207.15, 305.3

[56] References Cited

U.S. PATENT DOCUMENTS

| | | | |
|---|---|---|---|
| 1,273,542 | 7/1918 | Schooler | 604/264 |
| 1,879,249 | 9/1932 | Honsaker | 604/280 |
| 2,116,083 | 5/1938 | Rusch | 164/125 |
| 2,338,800 | 1/1944 | Burke | 604/117 |
| 2,458,305 | 1/1949 | Sanders | 604/282 |
| 2,568,566 | 9/1951 | Sokolik | 128/240 |
| 2,634,726 | 4/1953 | Hanson | 604/411 |
| 2,935,068 | 5/1960 | Donaldson | 128/348 |
| 3,154,079 | 10/1964 | McKay | 128/348 |
| 3,154,080 | 10/1964 | Rowan et al. | 128/349 |
| 3,589,368 | 6/1971 | Jackson et al. | 128/350 |
| 3,788,328 | 1/1974 | Alley et al. | 128/350 R |
| 3,890,970 | 6/1975 | Gullen | 128/215 |
| 3,903,895 | 9/1975 | Alley et al. | 128/350 R |
| 4,002,174 | 1/1977 | Reed et al. | 604/117 |
| 4,068,663 | 1/1978 | D'Alessandro | 604/275 |
| 4,129,129 | 12/1978 | Amrine | 128/214 R |
| 4,316,459 | 2/1982 | Walski | 128/207.17 |
| 4,329,985 | 5/1982 | Bonchek | 604/53 |
| 4,351,336 | 9/1982 | Sneider | 604/275 |
| 4,419,095 | 12/1983 | Negergall et al. | 604/96 |
| 4,490,139 | 12/1984 | Huizenga et al. | 604/264 |
| 4,496,353 | 1/1985 | Overland et al. | 604/280 |
| 4,548,597 | 10/1985 | Nelson | 604/43 |
| 4,561,445 | 12/1985 | Berke et al. | 604/274 |
| 4,596,548 | 6/1986 | De Vries et al. | 604/264 |
| 4,666,438 | 5/1987 | Raulerson | 604/272 |
| 4,680,029 | 7/1987 | Ranford et al. | 604/264 |

FOREIGN PATENT DOCUMENTS

| | | |
|---|---|---|
| 2936655 | 3/1980 | Fed. Rep. of Germany. |
| 0721166 | 2/1932 | France ............ 604/282 |

OTHER PUBLICATIONS

USCI, Extracorporeal Circulation Cannulae and Vinyl Specialty Catheters Catalogue, Section 7.

Corpak advertisement—Corpak Company, Wheeling, Ill. 80090.

*Primary Examiner*—Dalton L. Truluck
*Assistant Examiner*—Denise Whelton
*Attorney, Agent, or Firm*—Stanley N. Garber; Andrew J. Beck; William R. O'Meara

[57] ABSTRACT

A cannula for insertion into a body incision is provided with a tip having an opening in the sidewall and a pair of recesses in the outer surface of the tip forming a longitudinally extending ridge on one side on the tip for facilitating the insertion of the tip into the incision and dilating the incision.

3 Claims, 2 Drawing Sheets

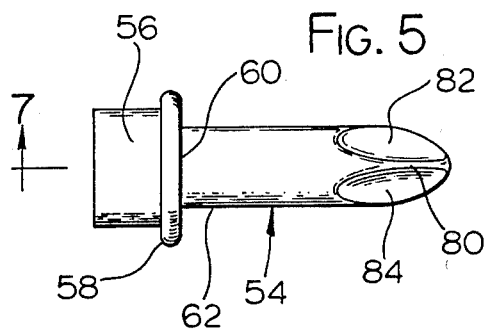
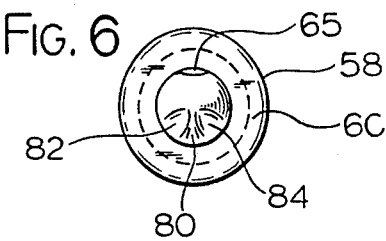
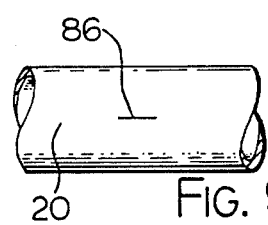
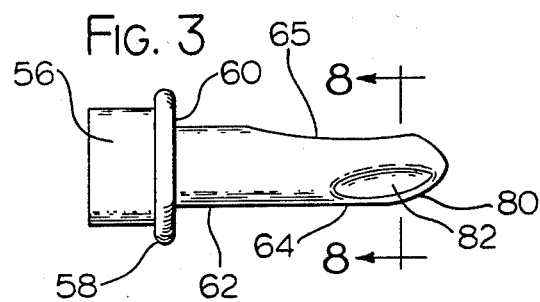
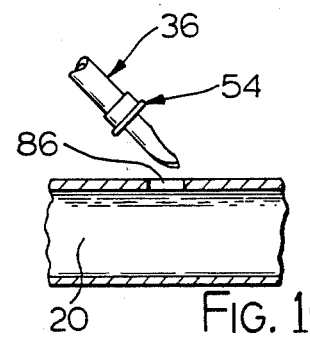
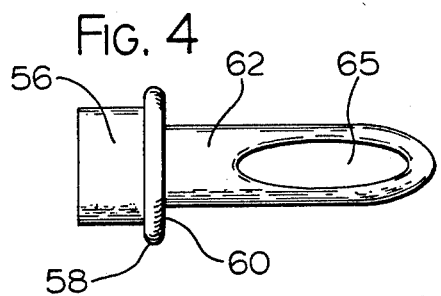
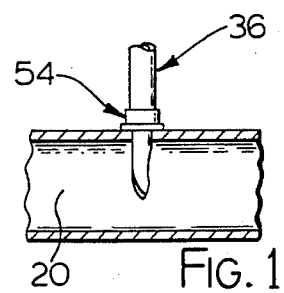
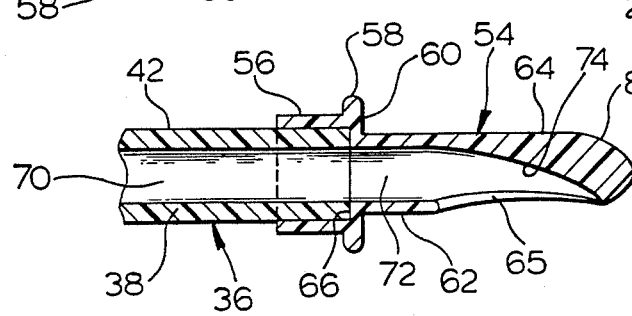
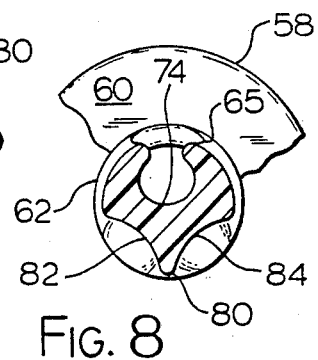

MEDICAL TUBE DEVICE

DESCRIPTION

1. Technical Field

This invention relates to medical tube device such as catheters and cannulas and more particularly to a medical tube adapted for insertion through an incision formed in a patient.

2. Background Art

Aortic cannulas which are often used during cardiac surgery, generally have a somewhat flexible elongate tube with a relatively rigid tip at the distal end of the cannula which is forced through an incision in the wall of the aorta to effect communication between the aorta and an extracorporeal circulation system. The extracorporeal system generally includes artificial heart-lung apparatus. For example, an aortic cannula can be employed in a total bypass system in which the heart is completely bypassed so that the heart or other organs and vessels can be operated on in a dry state.

One problem associated with conventional aortic cannulas has been that the distal tip of the cannula is rather difficult to insert through the incision and into the aorta without damage to the aorta. Generally the tip is rounded and blunt so that the slit or incision in the wall of the aorta tends to be traumatized as the blunt end enters the slit and moves into the aorta. If the incision is made large enough to reduce trauma during insertion of the cannula tip, then there is of course, greater damage to the patient due to the enlarged slit, and such slit requires a greater number of stitches. Also, use of a conventional aortic cannula generally produces considerable blood leakage due to the forces required to enter the incision or due to the fact that the incision is made large in an attempt to reduce the force required to enter the aorta. In some cases, open-ended cannulas are employed. When an openended cannula is used the edge of the wall about the end opening tends to catch on the edge of the incision and may produce damage. Some open-ended aortic cannulas have angled ends for effecting a change in the direction of blood flow from the cannula to the aorta. Such angled end devices, however, must be manipulated for proper orientation during insertion and may cause further damage to the aorta.

SUMMARY OF THE INVENTION

It is therefore an object of the present invention to provide a medical tube having an improved distal end adapted for insertion through an incision in a patient and wherein one or more of the above-mentioned problems or disadvantages are overcome.

Another object of the present invention is to provide an improved aortic perfusion cannula having an improved tip whereby trauma to the patient during insertion of the tip through an incision is minimized, and the force required to pass the tip through the incision is reduced, and blood leakage is reduced.

SUMMARY OF THE INVENTION

In accordance with one aspect of the present invention, a medical tube device is provided which includes an elongate tube having a distal end tip for insertion into an incision in a patient. The distal end tip has an outer axially extending ridge which aids insertion and reduces trauma to the patient.

These as well as other objects and advantages of the present invention, will become apparent from the following detailed description and accompanying drawings.

BRIEF DESCRIPTION OF THE DRAWINGS

FIG. 3 is an enlarged view of the distal cannula tip of the cannula device as shown FIG. 2 but alone;

FIG. 4 is a top view of the cannula tip shown in FIG. 3;

FIG. 5 is a bottom view of the cannula tip shown in FIG. 3;

FIG. 6 is a right end view of the tip as viewed in FIG. 3;

FIG. 7 is a longitudinal cross-sectional view taken along line 7—7 of FIG. 5 but with the cannula tip attached to the distal end of the cannula tube of FIG. 2;

FIG. 8 is a cross-sectional view taken along line 8—8 of FIG. 3;

FIG. 9 is an enlarged plan view of a portion of the aorta shown in FIG. 1 but prior to the insertion of the cannula;

FIG. 10 illustrates one manner of inserting the cannula into an incision in the aorta, the cannula being shown just before entering the incision; and FIG. 11 shows the cannula after it is fully inserted into the aorta.

DETAILED DESCRIPTION OF THE PREFERRED EMBODIMENT

Figure 1:
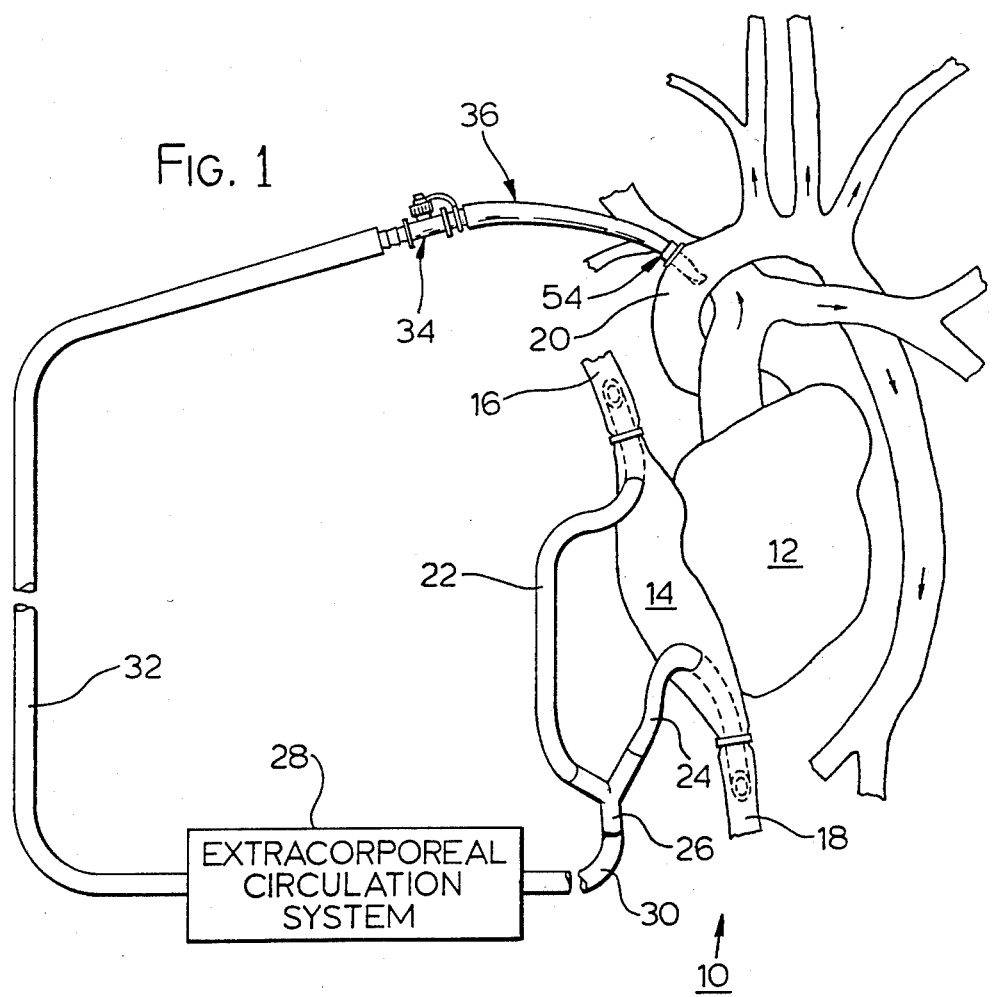
FIG. 1 is a diagrammatic illustration of a human heart and some associated blood vessels connected into an extracorporeal circulation system and employing an aortic cannula device in accordance with the present invention.

Referring now to the drawings, and particularly to FIG. 1, there is illustrated a portion of a surgical site 10 showing a heart 12, a right atrium 14, superior and inferior vena cavae 16 and 18 respectively, and an aorta 20 of a patient. A pair of vena caval catheters 22 and 24 extend into the atrium 14 and into the vena cavae 16 and 18, respectively. The vena cavae may be tightened about the ends of the catheters 22 and 24 by suitable string or the like. The opposite ends of the vena caval catheters 22 and 24 are connected to a Y-connector 26 connected to the inlet of an extracorporeal circulation system 28 through a tube 30. Thus venus blood is fed into a suitable or conventional extracorporeal system 28, for example, one that includes a blood oxygenator, blood pump, filters, bubble removing apparatus, and a defoamer. System 28 serves as an artificial heart and lung, changing venus blood into suitable oxygenated blood at the output of the system 28. A tube 32 connected to the outlet side of the circulation system 28 is connected through a tube connector 34 to an aortic cannula 36 shown inserted into the aorta 20 for returning oxygenated blood to the arterial system of the patient. The extracorporeal circulation system in FIG. 1, completely bypasses the heart so that the heart or associated organs and vessels may be operated on in the dry state.

Figure 2:
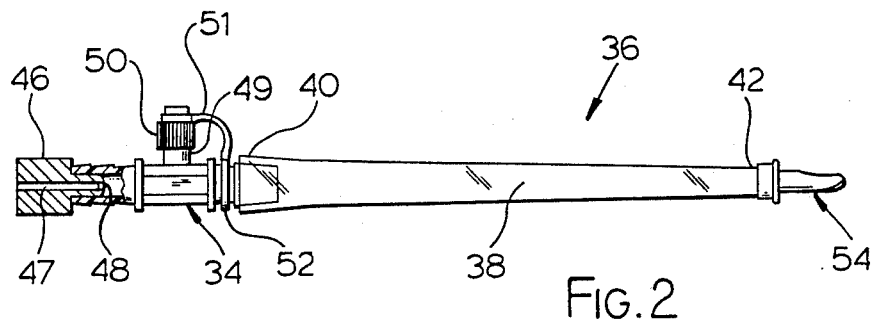
FIG. 2 is an enlarged side view of the aortic cannula device of FIG. 1 but with a tube connector attached thereto.

The aortic cannula 36, as seen in FIG. 2, includes a tube 38 tapering slightly from the proximal or left end 40 radially inwardly in the distal direction to the right or distal end 42. A hollow tube connector 34 has one end inserted into the proximal end 40 of tube 38 in tight sealing frictional engagement with it. A removable end cap or filter member 46 is shown in sealing engagement in the proximal end of connector 34. The member 46 is shown having a passage 47 extending through it. A hydrophobic filter 48 is shown covering the distal end of passage 47 while the proximal end of the passage is open to the atmosphere. The filter member 46, as will be further described, allows air originally in the cannula 36 to be purged from the cannula during insertion procedures but prevents blood from flowing through the filter. The tube connector 34 is provided with a side port 49 that is shown closed by a cap 50 which is tethered by a resilient strap 51 having an eyelet 52 surrounding the connector 34. The port 49 may be provided with a conventional luer tapered inner wall (not shown) for subsequent connection with a luer tapered syringe tip where it is desired to withdraw a sample of blood from the patient. Also, the port 49 may be provided with conventional luer lock ears and the inner wall of cap 50 provided with complementary luer lock threads so that cap 50 can be threaded onto and off of connector 34 as desired.

Cannula 36 includes a distal end tip 54 connected to the distal end 42 of tube 38. Preferably, cannula tip 54 is formed or molded as a separate plastic element and attached to the catheter 38. The catheter 38 may be made of a suitable plastic, preferably one that is flexible enough to allow some bending but which does not easily kink and occlude tube 38 when moderate bending forces are applied to it, such as during the connection of the cannula in the circulation system. Tube 38 may be formed of a suitable plastic or rubber, for example, may be formed of a thermoplastic material, such as polyvinyl chloride. The tip 54 may also be formed of a suitable material, for example, the same material as tube 38 but preferably of a somewhat harder or more rigid material so that it can be inserted into the aorta without bending. Tip 54 may be molded, for example, from a relatively rigid polyvinyl chloride.

Referring especially to FIGS. 3-8, cannula tip 54 includes an annular collar 56 having an annular flange 58 that has a distally facing flat side 60 and may be provided with suture slots if desired for securing the tip to the aorta. Collar 56 is integrally connected with a distally extending, generally cylindrical portion 62 of the tip which smoothly connects with a distal end portion 64. An elongate or generally eliptical opening 65 (FIG. 4) is provided in the sidewall of the tip. As best seen in FIG. 7, the distal end portion 42 of tube 38 is shown extending into collar 56 and engaging an inner radially inwardly extending annular wall or land 66 on the interior side of tip 54. The radially inner wall of the collar 56 and the outer wall of the tube 38 may be fixed together, such as by an adhesive, solvent bonding, or by other suitable means. Preferably, and as shown for illustration in FIG. 7, the thickness of the sidewall of tube 38 at the distal end is substantially the same as the width of the annular land 66 so that the tube lumen, indicated at 70, and the lumen of the cylindrical portion 62 of the tip, indicated at 72, are substantially the same so as to provide a smooth transition for blood flow from the tube 38 to the tip 54 where the tip is a separate part attached to the tube.

The distal end portion 64 of tip 54 has an inner preferably smoothly curving wall 74 (FIG. 7) extending between the inner wall of the cylindrical portion 62 and the distal end of opening 65 so that blood flowing distally in lumen 70 flows into the tip 54 and against the smoothly curving wall 74 and out the opening 65 with minimal turbulence even though there is a substantial angular change in the direction of blood flow. The wall 74 closes the distal end of the tip 54 and directs the flow of blood out opening 65.

The distal end portion 64 of tip 54 is provided with a smoothly contoured ridge 80 in the outer surface of the tip formed by two smoothly curving generally elliptical cavities or recesses 82 and 84 in the outer surface of the tip on opposite sides and adjacent the ridge 80. Ridge 80 smoothly blends into the cylindrical portion 62 of the tip as well as the distal extremity of the tip. The ridge 80 and recesses 82 and 84 have smoothly curving edges as best seen in FIG. 8, that is, the outer surface of the tip is free of any sharp edge. One or both of the edges of the opening 65 may be radiused or rounded to smoothly blend with the outer surface of the tip. The recesses 82 and 84 extend generally parallel to each other and angularly relative to the longitudinal axis of the tube and tip and radially inwardly toward the distal end surface of the tip. In this way, the exterior surfaces of the tip adjacent each side of the ridge 80 taper radially inwardly toward the distal end surface. The distal end surface of the tip thus narrows toward the distal end surface and is rounded or substantially free of sharp edges. The radially outermost surface of the ridge 80, as best seen in FIG. 3 and 7, is coextensive with the outer surface of the cylindrical portion 62 of the tip.

Preparatory to insertion, an incision or a slit 86, as shown in FIG. 9, may be made in the aorta 20. Preferably, with the ridge 80 at the bottom of the tip, the ridge is moved toward the slit as shown in FIG. 10, the cannula being held at an angle to the longitudinal axis of the aorta. As the ridge enter the slit, the slit is opened gradually or dilated until the entire tip penetrates the wall of the aorta. The cannula is then moved into the aorta until the annular distal side 60 of the flange 58 engages the outer surface of the aorta as shown in FIG. 11.

Upon insertion of the tip into the aorta 20, blood from the aorta flows into the cannula 36 displacing the air in the cannula 36 and causing the air to flow through the filter pasage 47 to the atmosphere. The hydrophobic filter 48 will not allow blood to pass through it. With the air removed from the cannula, filter 46 is removed and the proximal end of connector 34 may be connected to the tube 32 (FIG. 1). The tube 38 may conveniently be clamped off during removal of the cap and the connection of tube 32 to tube 38. If further air is found in the cannula 36 or connector 34, it may be removed by removing the cap 50 to vent such air to the atmosphere. Also, the side part 49 which may be in the form of a luer lock connector may be used to take a blood sample by inserting a syringe into port 49 and withdrawing a blood sample.

By providing the longitudinally extending smoothly blending ridge 80, the ridge can be used as the leading edge of the cannula during insertion into the aorta so that the forces applied are more evenly distributed in spreading the walls of the incision so as to reduce trauma to the aorta and reduce blood loss. Upon insertion of tip 54, the slit will tend to be dilated and conform closely to the outer wall of the cylindrical portion 62 through the incision to reduce blood loss. Furthermore, the distal sidewall 60 of flange 58 can be urged against the outer surface of the aorta such as by suturing or tying tending to further prevent blood flow through the incision. Thus, use of the cannula 38 can effect a reduced amount of blood loss during insertion of the cannula into the aorta as well as reduce continued blood loss during the operation. Furthermore, there is less trauma or damage to the patient because of the tapered shape and ridge 80 of the tip 54 which gradually dilate the incision as previously pointed out. By providing smoothly curving wall sections and eliminating sharp edges, blood can flow through the cannula with reduced hemolysis.

As various changes could be made in the above construction without departing from the scope of the invention, it is intended that all matter contained in the above description and apparatus shown in the accompanying drawings shall be interpreted as illustrative and not in a limiting sense.

What is claimed is:

1. An aortic cannula for insertion into an incision made in an aorta of a patient for connecting the aorta into an extra corporeal blood circulation system comprising a plastic tube having a lumen extending therethrough and proximal and distal ends, means for connecting the proximal end of said tube intot he extracorporeal blood circulation system, and a generally tubular plastic tip having a proximal end connected to the distal end of said tube, said tip having a lumen connected with said tube lumen and an opening through the sidewall thereof for the flow of blood therethrough, said tip lumen having a distal end wall closing the distal end thereof and smoothly curving from the sidewall of said tip lumen to the distal end of said opening, said tip having a pair of elongate recesses in the outer surface thereof adjacent the distal end thereof defining a generally external axially extending ridge between said recesses for moving the walls of the aorta apart at the incision, said ridge having smoothly rounded generally axially extending edges smoothly blending into the outer surface of the distal end of said tip, said opening being the only opening in the sidewall of said tip, said ridge being located on the side of said tip opposite the side that includes said opening and is the only ridge on said tip, said tip having a generally cylindrical portion proximally of the proximal end of said opening, the radially outermost surfaces of said cylindrical portion and of said ridge being substantially radially equidistant from the longitudinal axis of said tip, said tip being of a relatively hard material such that the material maintains said tip in a fixed shape during use, the distal end of said tip having an outer smoothly curving surface between the distal end of said opening and the distal end of said ridge, and a flange connected to said cylindrical portion extending radially outwardly therefrom and located a predetermined distance from the distal end surface of said tip to limit the distance of insertion of said tip into the aorta wherein said recesses are inwardly concave.

2. The cannula of claim 1 wherein said recesses are substantially eliptical with their longer axes extending generally inwardly and toward the distal end of said tip.

3. The cannula of claim 2 wherein said recesses are arcuate in cross-section.

* * * * *